US009621776B2

(12) United States Patent
Ono et al.

(10) Patent No.: US 9,621,776 B2
(45) Date of Patent: Apr. 11, 2017

(54) IMAGING ELEMENT, IMAGING DEVICE AND ENDOSCOPE SYSTEM

(71) Applicant: OLYMPUS CORPORATION, Tokyo (JP)

(72) Inventors: Makoto Ono, Sagamihara (JP); Nana Akahane, Hachioji (JP); Masashi Saito, Akishima (JP); Yoshio Hagihara, Tokyo (JP); Susumu Yamazaki, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/847,226

(22) Filed: Sep. 8, 2015

(65) Prior Publication Data

US 2015/0381866 A1 Dec. 31, 2015

Related U.S. Application Data

(63) Continuation of application No. PCT/JP2014/059456, filed on Mar. 31, 2014.

(30) Foreign Application Priority Data

Apr. 18, 2013 (JP) .................................. 2013/087615

(51) Int. Cl.
*H04N 5/335* (2011.01)
*H04N 5/225* (2006.01)
(Continued)

(52) U.S. Cl.
CPC ....... *H04N 5/2256* (2013.01); *A61B 1/00018* (2013.01); *A61B 1/045* (2013.01); *H04N 5/23241* (2013.01); *H04N 2005/2255* (2013.01)

(58) Field of Classification Search
CPC ...... H04N 5/378; H04N 3/155; H04N 5/3742; H04N 5/3575; H04N 5/3745; H04N 5/376;
(Continued)

(56) References Cited

U.S. PATENT DOCUMENTS 5,296,696 A 3/1994 Uno
5,942,774 A * 8/1999 Isogai ............... H01L 27/14603
257/257

(Continued)

FOREIGN PATENT DOCUMENTS

JP S62-185471 A 8/1987
JP H05-207220 A 8/1993
(Continued)

OTHER PUBLICATIONS

International Search Report dated Jul. 1, 2014 issued in PCT/JP2014/059456.
(Continued)

*Primary Examiner* — Nathnael Aynalem
(74) *Attorney, Agent, or Firm* — Scully, Scott, Murphy & Presser, P.C.

(57) ABSTRACT

An imaging element includes: a plurality of pixels configured to receive light from outside and generate and output an imaging signal depending on an amount of the light received; a first transfer line connected to the pixel; a second transfer line; a column selection switch configured to select one pixel column and output the imaging signal to the second transfer line; a column source follower including a gate to which the imaging signal transferred by the first transfer line is input, a drain end being connected to a power supply voltage, and a source end being connected to the column selection switch; a constant current source configured to drive the column source follower and read out the
(Continued)

imaging signal to the second transfer line; and a current generating unit configured to flow a predetermined current to the source end side of the column source follower.

9 Claims, 12 Drawing Sheets

(51) Int. Cl.
*A61B 1/00* (2006.01)
*A61B 1/045* (2006.01)
*H04N 5/232* (2006.01)

(58) Field of Classification Search
CPC .... H04N 5/374; H04N 5/3577; H04N 5/3698; H04N 5/3741; H04N 2005/2255; H04N 5/335; H04N 5/363; H04N 5/365; H04N 5/3658; H04N 3/1512; H04N 3/1581; H04N 5/2173; H04N 5/23203; H04N 5/357; H04N 5/3595; H04N 5/37457; H04N 3/1593; H04N 3/1568; H04N 5/2175; H01L 27/14887
USPC .. 348/65, 241, 272, 281–283, 298–302, 314
See application file for complete search history.

(56) References Cited

U.S. PATENT DOCUMENTS

| | | | |
|---|---|---|---|
| 6,600,160 B2 * | 7/2003 | Kobayashi | H01L 27/14659 250/370.09 |
| 6,674,470 B1 * | 1/2004 | Tanaka | H04N 3/155 348/302 |
| 6,801,256 B1 | 10/2004 | Egawa et al. | |
| 6,903,768 B1 * | 6/2005 | Ohsawa | H04N 5/3658 348/222.1 |
| 6,965,408 B2 * | 11/2005 | Hiyama | H04N 3/155 348/308 |
| 6,989,863 B1 * | 1/2006 | Takahashi | H01L 27/146 257/E27.13 |
| 7,352,020 B2 | 4/2008 | Yamaguchi | |
| 7,569,820 B2 | 8/2009 | Iida | |
| 2001/0033337 A1 * | 10/2001 | Sakuragi | H04N 5/32 348/302 |
| 2002/0044271 A1 | 4/2002 | Leigh-Jones et al. | |
| 2002/0158982 A1 * | 10/2002 | Kokubun | H04N 5/343 348/308 |
| 2003/0025816 A1 * | 2/2003 | Sakuragi | H04N 5/3653 348/301 |
| 2004/0057719 A1 * | 3/2004 | Ogura | H01L 27/14618 396/439 |
| 2009/0001275 A1 | 1/2009 | Okada | |
| 2011/0115958 A1 | 5/2011 | Koseki et al. | |
| 2011/0242390 A1 | 10/2011 | Sogoh et al. | |
| 2011/0279720 A1 * | 11/2011 | Nakagawa | H04N 5/3745 348/300 |
| 2012/0092536 A1 | 4/2012 | Hirota | |
| 2013/0057754 A1 | 3/2013 | Shimada et al. | |
| 2013/0083227 A1 | 4/2013 | Murata et al. | |

FOREIGN PATENT DOCUMENTS

| | | |
|---|---|---|
| JP | H09-247538 A | 9/1997 |
| JP | H10-136266 A | 5/1998 |
| JP | 2000-050167 A | 2/2000 |
| JP | 2000-059691 A | 2/2000 |
| JP | 2001-078098 A | 3/2001 |
| JP | 2001-251555 A | 9/2001 |
| JP | 2004-282236 A | 10/2004 |
| JP | 2006-121652 A | 5/2006 |
| JP | 2010-056915 A | 3/2010 |

OTHER PUBLICATIONS

Japanese Notice of Rejection, dated Jan. 27, 2015 issued in JP 2014-555890.
Japanese Decision of a Patent Grant dated Jun. 2, 2015 issued in JP 2014-555890.
Decision of a Patent Grant dated Jun. 28, 2016 in related Japanese Patent Application No. 2015-128132.
Extended Supplementary European Search Report dated Oct. 21, 2016 in related European Patent Application No. 14 78 5730.4.

* cited by examiner

IMAGING ELEMENT, IMAGING DEVICE AND ENDOSCOPE SYSTEM

CROSS-REFERENCE TO RELATED APPLICATIONS

This application is a continuation of PCT international application Ser. No. PCT/JP2014/059456 filed on Mar. 31, 2014 which designates the United States, incorporated herein by reference, and which claims the benefit of priority from Japanese Patent Applications No. 2013-087615, filed on Apr. 18, 2013, incorporated herein by reference.

BACKGROUND OF THE INVENTION

1. Field of the Invention

The present invention relates to an imaging element, an imaging device and an endoscope system.

2. Description of the Related Art

Conventionally, a technique of providing a noise elimination unit for each pixel column has been known for imaging devices having complementary metal-oxide semiconductor (CMOS) image sensors, in order to eliminate a fixed pattern noise due to variation of transistors among pixels and a reset noise of charge-voltage conversion units within unit pixels (for example, see Japanese Laid-open Patent Publication No. 2000-059691 and Japanese Laid-open Patent Publication No. 2006-121652).

FIG. 12 is a circuit diagram illustrating a configuration of a conventional imaging device. In this example, a description will be made regarding a case in which an imaging device 500 has a CMOS image sensor.

The imaging device 500, for example, is arranged at a distal end portion of an endoscope and includes a light receiving unit and a reading unit. The light receiving unit is configured of a plurality of unit pixels 530, which are arranged in a two dimensional matrix form over a plurality of rows and a plurality of columns, and a plurality of vertical transfer lines 539, each of which is provided for each column of the two-dimensional matrix and transfers a signal output from each of the unit pixels 530. The reading unit is configured of a vertical scanning unit (row selection circuit) 541, a pixel drive line 549, which supplies a drive signal from the vertical scanning unit 541 to each of the unit pixels 530, a noise elimination unit 543, which is provided for each pixel column, and a horizontal scanning unit (column selection circuit) 558.

Each of the unit pixels 530 includes: a photoelectric conversion element, which accumulates a signal charge depending on the amount of incident light; a charge conversion unit, which performs voltage conversion on the signal charge transferred from the photoelectric conversion element; a transfer transistor, which transfers the signal charge from the photoelectric conversion element to the charge conversion unit; a reset transistor, which resets the signal charge transferred to the charge conversion unit; a row selection transistor; and an output transistor, which outputs an imaging signal to the vertical transfer line 539.

The reading unit turns the row selection transistor of an arbitrary row into an ON state by the vertical scanning unit (row selection circuit) 541 and reads out the imaging signal to the vertical transfer line 539. The read out imaging signal is input to the noise elimination unit 543 and a noise component thereof is eliminated. Thereafter, the imaging signal is output as image information to outside by the horizontal scanning unit 558.

FIG. 13 is a circuit diagram illustrating a configuration of the noise elimination unit of the imaging device illustrated in FIG. 12. The noise elimination unit 543 includes: a transistor 544 for sampling and holding, with one end side thereof connected to the vertical transfer line 539; a coupling condenser (AC coupling capacitor) CC with one end side thereof connected to the other end side of the transistor 544; a charge accumulation condenser (sampling capacitor) CS, which is connected between the other end side of the AC coupling capacitor CC and ground; and a potential clamp transistor 545, which is connected to a connection node SN between the AC coupling capacitor CC and the sampling capacitor CS. The connection node SN is connected to the horizontal scanning unit 558 including a column selection transistor.

First, the noise elimination unit 543 turns the transistor 544 for sampling and holding into an ON state at the time of pixel resetting, transmits a noise signal transferred by the vertical transfer line 539 using the AC coupling capacitor CC, turns the potential clamp transistor 545 into an ON state for a predetermined time period, and samples a noise signal level in the sampling capacitor CS. Thereafter, at the time of reading out the imaging signal, the imaging signal including the noise signal (light-noise sum signal) is transmitted by the AC coupling capacitor CC again. Since a voltage change of the imaging signal after the pixel resetting is transmitted, as a result, it is possible to take out, from the light-noise sum signal, the imaging signal from which the noise signal has been subtracted.

The noise elimination unit 543 illustrated in FIG. 13 requires two condensers of the AC coupling capacitor CC and the sampling capacitor CS for each pixel column. When the number of pixels increases, a size of the condenser becomes a constraint to make miniaturization of the imaging device difficult. In addition, a gain is reduced due to capacity division between the AC coupling capacitor CC and the sampling capacitor CS when the signal level is sampled, and thus, the S/N ratio deteriorates. In order to suppress such a problem, it is necessary to increase a size of the AC coupling capacitor CC, and then, the miniaturization of the imaging device becomes further difficult.

In order for the miniaturization of the imaging device, it is possible to consider decreasing a capacity of the sampling capacitor CS. In the CMOS image sensor, there is a case in which a leakage current is generated in the column selection transistor or the like so that a noise is superimposed on the imaging signal read out to a horizontal transfer line. The column selection transistor selects a pixel matrix for column by column and reads out the imaging signal to the horizontal transfer line, and thus, there occurs a time difference between a column read out at the first time and a column read out at the last time. Since the leakage current is accumulated and superimposed on the imaging signal during such a time difference, so-called shading such as generation of unevenness in luminance in a horizontal direction is generated. In a case where the capacity of the sampling capacitor CS is sufficient, it is possible to absorb the influence of noise caused by the leakage current or the like, but the influence of noise caused by the leakage current or the like on the imaging signal becomes greater and an image quality becomes worse as the capacity becomes smaller.

There is a need for an imaging element, an imaging device and an endoscope system capable of achieving miniaturization without deterioration in image quality.

SUMMARY OF THE INVENTION

An imaging element according to one aspect of the present invention includes: a plurality of pixels arranged in a two-dimensional matrix form, configured to receive light from outside, and configured to generate and output an imaging signal depending on an amount of the light received; a first transfer line connected to the pixel and configured to transfer the imaging signal; a second transfer line to which the imaging signal transferred by the first transfer line is output; a column selection switch configured to select one pixel column among the two-dimensional matrix, and output the imaging signal transferred by the first transfer line to the second transfer line; a column source follower including a gate to which the imaging signal transferred by the first transfer line is input, a drain end being connected to a power supply voltage, and a source end being connected to the column selection switch; a constant current source configured to drive the column source follower and read out the imaging signal transferred by the first transfer line to the second transfer line; and a current generating unit configured to flow a predetermined current to the source end side of the column source follower to absorb, by the column selection switch, an influence of noise caused by a leakage current.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
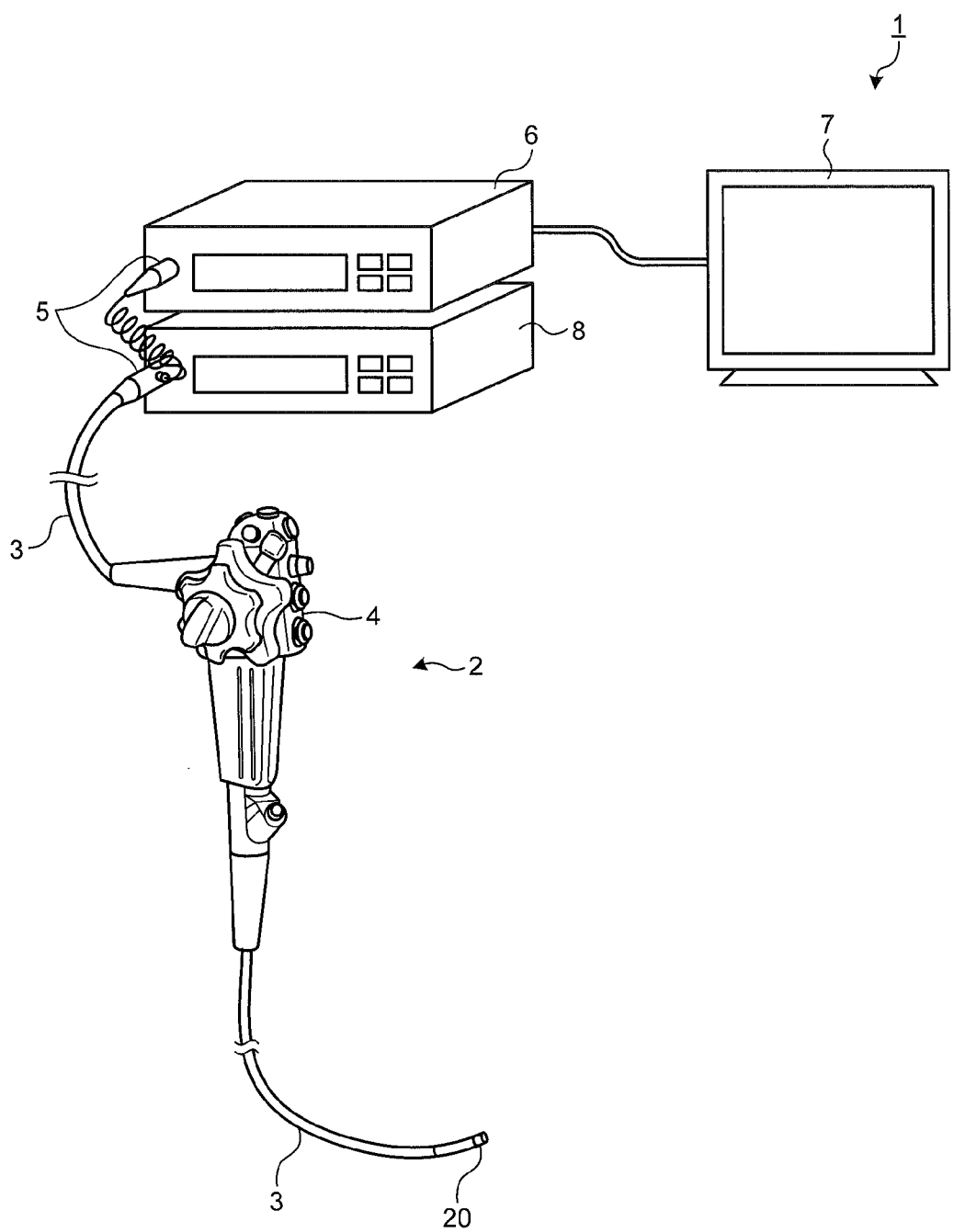
FIG. 1 is a diagram schematically illustrating the entire configuration of an endoscope system according to a first embodiment of the present invention.

In the following description, a description will be made regarding an endoscope system provided with an imaging device as modes for carrying out the present invention (hereinafter, referred to as "embodiments"). Further, the present invention is not limited by these embodiments. In addition, the same reference numerals are attached to the same portions in the description of the drawings. Moreover, the drawings are schematic, and it is necessary to note that the relation between the thickness and width of each component and the ratios among the respective components are different from the actual. In addition, portions with different sizes and ratios from each other are included among the drawings.

FIG. 1 a diagram schematically illustrating the entire configuration of an endoscope system according to a first embodiment of the present invention. An endoscope system 1, illustrated in FIG. 1, includes an endoscope 2, a transmission cable 3, a connector unit 5, a processor (control device) 6, a display device 7 and a light source device 8. The endoscope 2 captures an in-vivo image of a subject and outputs an imaging signal, by inserting an insertion portion, which is a part of the transmission cable 3, into a body cavity of the subject. The transmission cable 3 connects the endoscope 2 with the connector unit 5. The connector unit 5 is connected to the endoscope 2, the processor 6 and the light source device 8, performs analog-digital conversion (A/D conversion) on the imaging signal while performing predetermined signal processing on the imaging signal output from the connected endoscope 2, and outputs the converted imaging signal as an image signal. The processor 6 performs predetermined image processing on the image signal output from the connector unit 5 and controls the entire endoscope system 1. The display device 7 displays the image signal processed by the processor 6. The light source device 8 is, for example, configured by using a white LED. Pulsed white light lighted by the light source device 8 passes through the connector unit 5 and the transmission cable 3 and becomes illumination light to be irradiated towards the subject from a distal end side of the insertion portion of the endoscope 2.

The endoscope 2 is provided with an imaging unit (imaging device) 20 that captures the in-vivo images of the subject, at one end side of the transmission cable 3, which is the distal end side of the insertion portion to be inserted into the body cavity of the subject. An operation unit 4 that receives various operations with respect to the endoscope 2 is connected to a proximal end side of the insertion portion. The imaging unit 20 is connected to the connector unit 5, via the operation unit 4, by the transmission cable 3. The imaging signal of the image captured by the imaging unit 20 passes through the transmission cable 3 having a length of several meters, and is output to the connector unit 5, for example.

Figure 2:
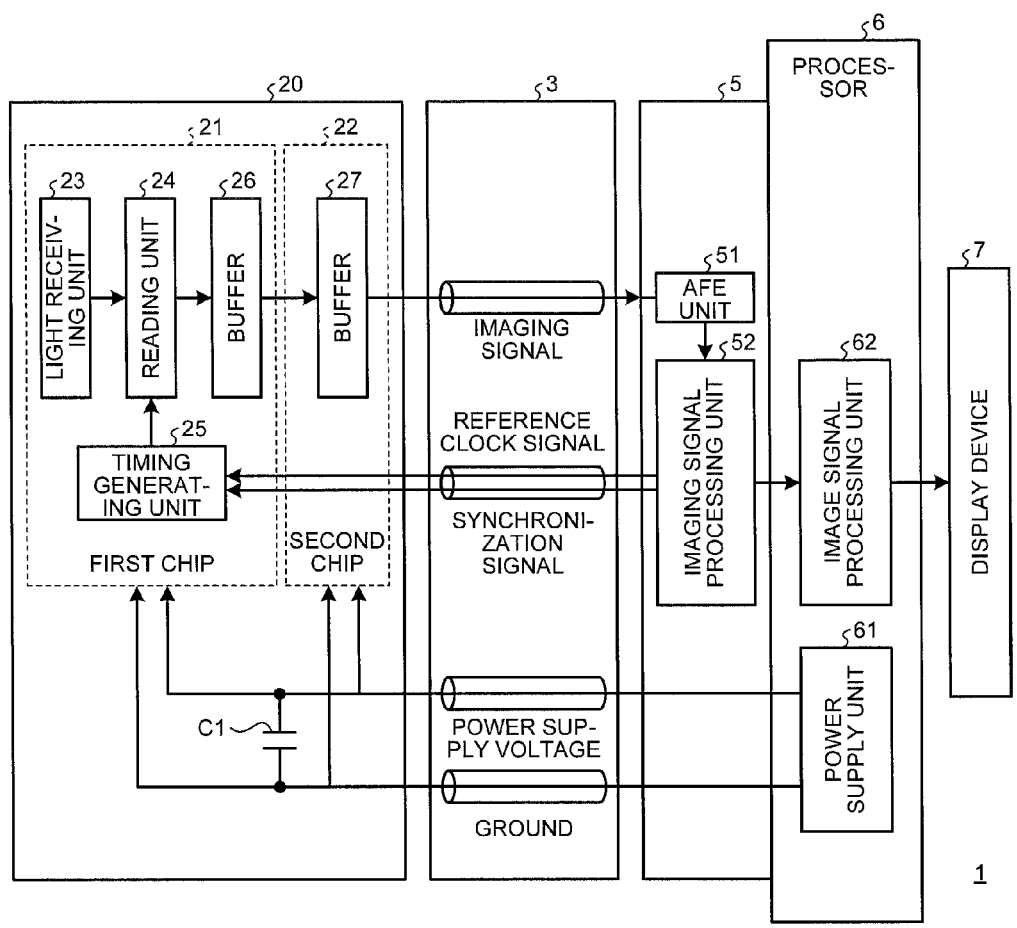
FIG. 2 is a block diagram representing a function of a main part of the endoscope system according to the first embodiment of the present invention.

FIG. 2 is a block diagram representing a function of a main part of the endoscope system according to the first embodiment of the present invention. A description will be made regarding details of each configuration of the endoscope system 1 and a route of an electrical signal inside the endoscope system 1 with reference to FIG. 2.

The imaging unit 20 includes a first chip 21 having a light receiving unit 23, and a second chip 22 having a buffer 27. The first chip 21 and the second chip 22 are bonded to be opposed to each other, and the chips are connected by pads arranged at peripheral edge portions of the chips, vias penetrating through the chips, or the like. Incidentally, the first chip 21 and the second chip 22 are not limited to those arranged such that principal planes thereof become parallel to each other, and may be arrange side by side or arranged such that with respect to the principle plane of one, the principle plane of the other one becomes vertical, depending on a structure of the surroundings.

The first chip 21 of the imaging unit 20 includes: the light receiving unit 23 in which multiple unit pixels are arranged in a two dimensional matrix form in both row and column directions; a reading unit 24 that reads out an imaging signal photoelectrically converted in the light receiving unit 23; a timing generating unit 25 that generates a timing signal based on a reference clock signal and a synchronization signal sent out from the connector unit 5 and supplies the timing signal to the reading unit 24; and a buffer (multiplexer) 26 that outputs the imaging signal to the second chip 22. A more detailed configuration of the first chip 21 will be described in detail later with reference to FIG. 3.

The second chip 22 of the imaging unit 20 includes a buffer 27 that functions as a transmission unit, which transmits only an alternating current component of the imaging signal output from the first chip 21 to the processor 6, via the transmission cable 3 and the connector unit 5. Incidentally, combinations of circuits to be mounted on the first chip 21 and the second chip 22 may be changed as appropriate in accordance with design conditions.

Further, the imaging unit 20 receives a power supply voltage (VDD) generated in a power supply unit 61 inside the processor 6, along with a ground (VSS), via the transmission cable 3. A condenser C1 for power supply stabilization is provided between the power supply voltage (VDD) and the ground (VSS) supplied to the imaging unit 20. The connector unit 5 includes an analog front end (AFE) unit 51 and an imaging signal processing unit 52. The connector unit 5 functions as a relay processing unit that electrically connects the endoscope 2 (imaging unit 20) with the processor 6 and relays an electrical signal. The connector unit 5 and the imaging unit 20 are connected to each other by the transmission cable 3 and the connector unit 5 and the processor 6 are connected by a coil cable, for example. Further, the connector unit 5 is connected also to the light source device 8.

The AFE unit 51 receives the imaging signal transmitted from the imaging unit 20, and performs impedance matching by a passive element such as a resistance, and thereafter, takes out an alternating current component by a condenser and determines an operation point by a voltage dividing resistance. Thereafter, the AFE unit 51 performs analog-digital (A/D) conversion on an analog imaging signal and transmits the converted signal as a digital imaging signal to the imaging signal processing unit 52.

The imaging signal processing unit 52 is configured of, for example, a field programmable gate array (FPGA), generates a reference clock signal (for example, a clock of 27 MHz) to be a reference of operation of each component of the endoscope 2 and a synchronization signal representing a start position of each frame, supplies the generated signals to the timing generating unit 25, and performs predetermined signal processing, such as noise elimination, on the digital imaging signal input from the AFE unit 51.

The processor 6 is configured by including the power supply unit 61 and an image signal processing unit 62, and is a control device that controls the entire endoscope system 1. The power supply unit 61 generates the power supply voltage (VDD) and supplies the generated power supply voltage, together with the ground (VSS), to the imaging unit 20, via the connector unit 5 and the transmission cable 3. The image signal processing unit 62 performs predetermined image processing on the digital imaging signal subjected to the signal processing, such as noise elimination, by the imaging signal processing unit 52, and outputs the processed signal as an image signal to the display device 7.

The display device 7 displays the image captured by the imaging unit 20, based on the image signal. Examples of the image processing in the image signal processing unit 62 include a synchronization process, a white balance (WB) adjustment process, a gain adjustment process, a gamma correction process, a digital-analog (D/A) conversion process, a format conversion process or the like.

Figure 3:
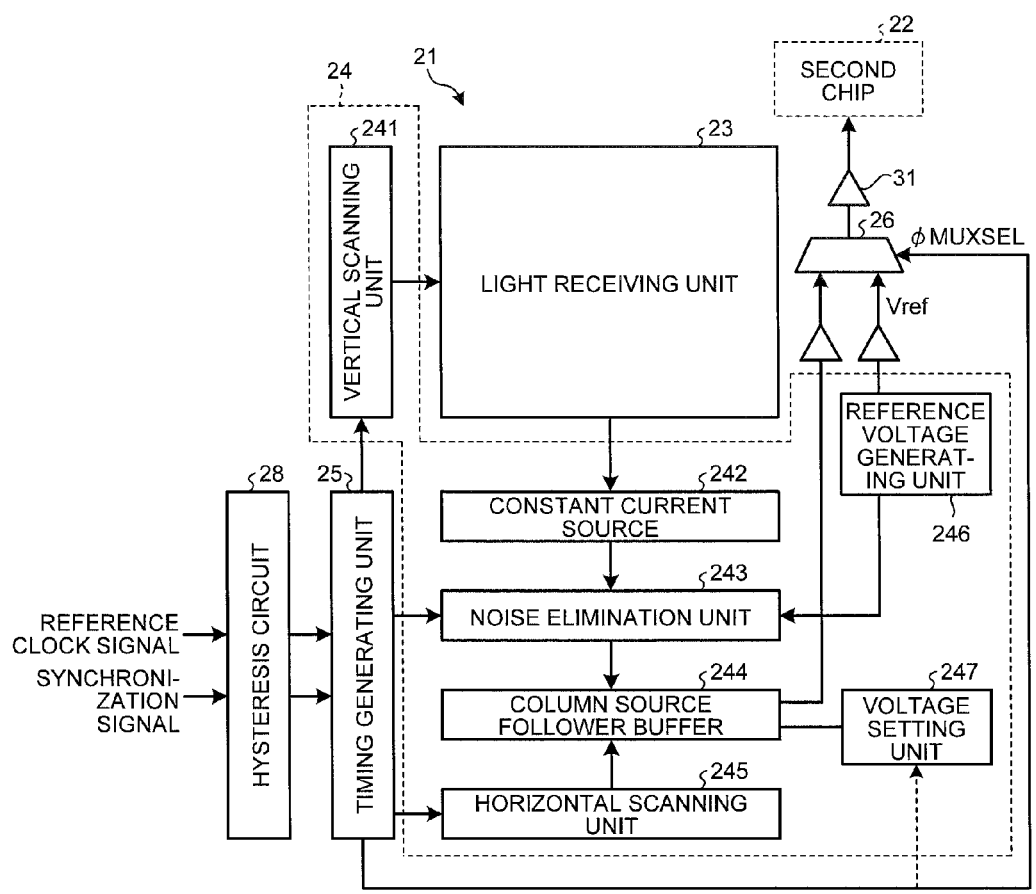
FIG. 3 is a block diagram illustrating details of a first chip illustrated in FIG. 2.
Figure 4:
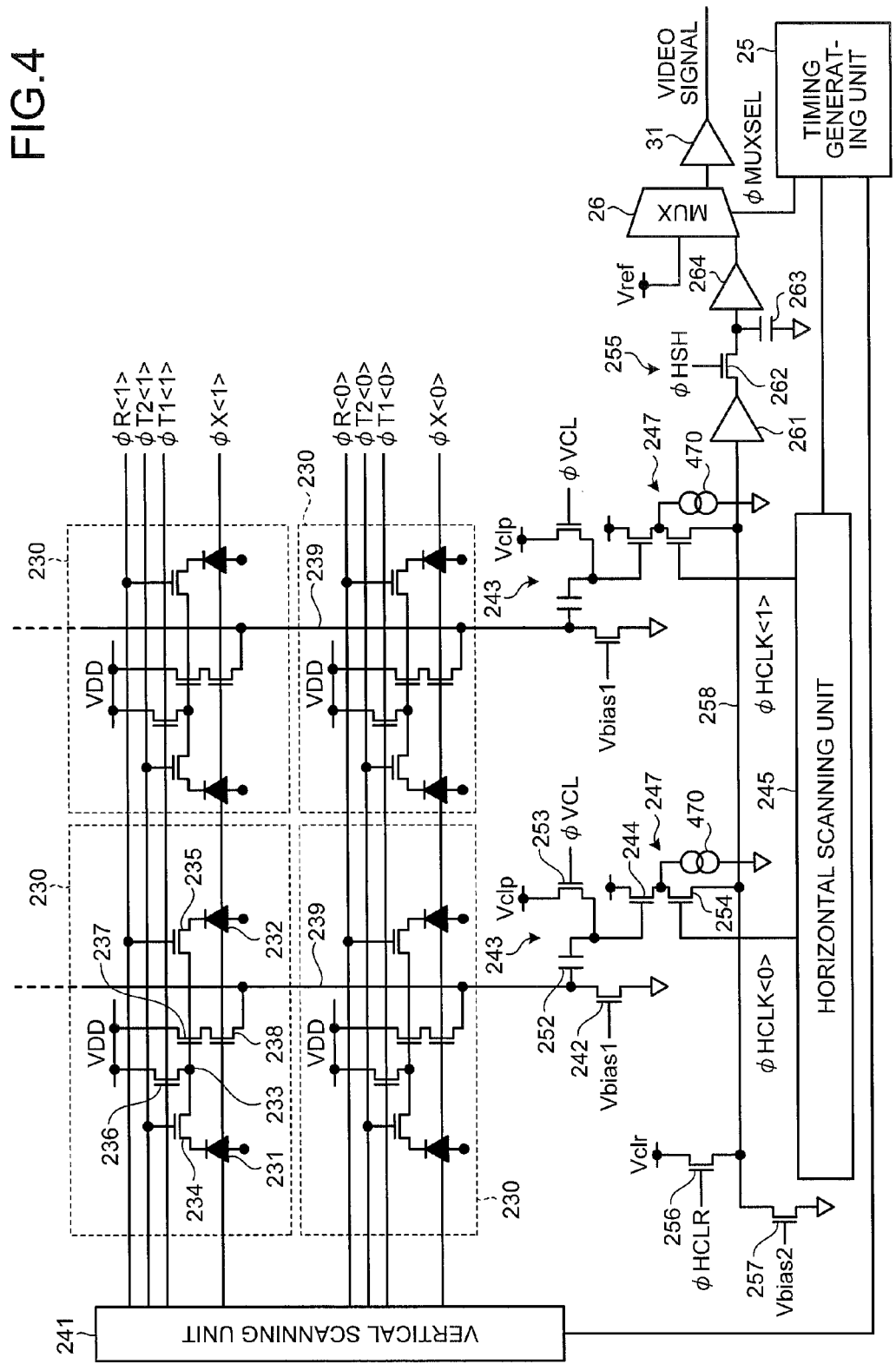
FIG. 4 is a circuit diagram illustrating a configuration of the first chip of the endoscope system according to the first embodiment.

FIG. 3 is a block diagram illustrating a detailed configuration of the first chip illustrated in FIG. 2. FIG. 4 is a circuit diagram illustrating a configuration of the first chip of the endoscope system according to the first embodiment. For example, the light receiving unit 23, the reading unit (drive unit) 24, the timing generating unit 25, and the multiplexer 26 are mounted on the first chip 21. Details of the light receiving unit 23 will be described later with reference to FIG. 4. A hysteresis circuit 28 is provided at a previous stage of the timing generating unit 25, that is, between an input of the timing generating unit 25 and the processor 6. The hysteresis circuit 28 performs waveform shaping of the reference clock signal and the synchronization signal transmitted over a long distance by the transmission cable 3. The reference clock signal and the synchronization signal subjected to the waveform shaping in the hysteresis circuit 28 are input to the timing generating unit 25.

The timing generating unit 25 generates various drive signals (φT1, φT2, φR, φX, φVCL, φHCLR, φHCLK, φMUXSEL or φVSH) based on the reference clock signal and the synchronization signal shaped by the hysteresis circuit 28, and supplies those drive signals to a vertical scanning unit 241, a noise elimination unit 243, a horizontal scanning unit 245, the multiplexer 26, and a reference voltage generating unit 246.

The reading unit 24 includes the vertical scanning unit (row selection circuit) 241, a constant current source 242, the noise elimination unit 243, a column source follower buffer (transistor) 244, the horizontal scanning unit (column selection circuit) 245, the reference voltage generating unit 246, and a voltage setting (potential setting) unit 247.

The vertical scanning unit 241 applies row selection pulses φT1<N>, φT2<N>, φR<N>, and φX<N> to a selected row <N> (N=0, 1, 2, . . . , n−1, n) of the light receiving unit 23, based on the drive signals (φT, φR, and φX) supplied from the timing generating unit 25 so as to drive each unit pixel 230 of the light receiving unit 23 by the constant current source 242, transfers the imaging signal and the noise signal at the pixel resetting to a vertical transfer line 239 and outputs the signals to the noise elimination unit 243.

The noise elimination unit 243 eliminates output variation for each unit pixel 230 and the noise signal at the pixel resetting, and outputs an imaging signal photoelectrically converted by each unit pixel 230 to the column source follower buffer 244. Incidentally, details of the noise elimination unit 243 will be described later with reference to FIG. 4.

The horizontal scanning unit 245 applies a column selection pulse φHCLK<M> to a selected column <M> (M=0, 1, 2, . . . , m−1, m) of the light receiving unit 23, based on the drive signal (φHCLK) supplied from the timing generating unit 25, and transfers the imaging signal photoelectrically converted by each unit pixel 230 to a horizontal transfer line 258 via the column source follower buffer 244 and outputs the imaging signal to the multiplexer 26.

The multiplexer 26 is driven by the drive signal (φMUXSEL) supplied from the timing generating unit 25, and alternately outputs the imaging signal input through the horizontal transfer line 258 and a reference voltage Vref (constant voltage signal) generated by the reference voltage generating unit 246 to the second chip 22, via an output unit (amplifier) 31. This output reference voltage Vref is used in the imaging signal processing unit 52 or the like of the connector unit 5 for elimination of in-phase noise superimposed in the transmission cable 3 during transmission of the imaging signal. Incidentally, an amplifier for gain adjustment may be provided at an input side of the multiplexer 26 if necessary.

Multiple unit pixels 230 are arranged in a two dimensional matrix form in the light receiving unit 23 of the first chip 21. Each of the unit pixels 230 includes photoelectric conversion elements 231 and 232, a charge conversion unit 233, transfer transistors (first transfer unit) 234 and 235, a pixel reset unit (transistor) 236, a pixel source follower transistor 237 and a pixel output switch (signal output unit) 238. Incidentally, in this specification, one or a plurality of the photoelectric conversion elements, and the transfer transistor for transferring a signal charge from each photoelectric conversion element to the charge conversion unit 233 are called a unit cell. That is, a set of one or the plurality of the photoelectric conversion elements, and the transfer transistor is included in the unit cell, and one unit cell is included in each unit pixel 230.

The photoelectric conversion elements 231 and 232 photoelectrically convert and accumulate incident light to a signal charge quantity corresponding to a light quantity thereof. Cathode sides of the photoelectric conversion elements 231 and 232 are connected, respectively, to one end sides of the transfer transistors 234 and 235, and anode sides thereof are connected to the ground VSS. The charge conversion unit 233 is formed of a floating diffusion capacitor (FD) and converts the charge accumulated in the photoelectric conversion elements 231 and 232 into voltage.

The transfer transistors 234 and 235 transfer the charge from the photoelectric conversion elements 231 and 232 to the charge conversion unit 233, respectively. Signal lines, to which the pulsed drive signals (row selection pulses) φT1 and φT2 are supplied, are respectively connected to gates of the transfer transistors 234 and 235, and the charge conversion unit 233 is connected to other end sides thereof. When the pulsed drive signals φT1 and φT2 are supplied from the vertical scanning unit 241 via the signal lines, the transfer transistors 234 and 235 are turned into an ON state and the signal charge is transferred from the photoelectric conversion elements 231 and 232 to the charge conversion unit 233.

The pixel reset unit (transistor) 236 resets the charge conversion unit 233 to a predetermined potential. One end side of the pixel reset unit 236 is connected to the power supply voltage VDD, the other end side thereof is connected to the charge conversion unit 233, and a signal line, to which the pulsed drive signal φR is supplied, is connected to a gate thereof. When the pulsed drive signal φR is supplied from the vertical scanning unit 241 via the signal line, the pixel reset unit 236 is turned into an ON state, the signal charge accumulated in the charge conversion unit 233 is released, and the charge conversion unit 233 is reset to the predetermined potential.

One end side of the pixel source follower transistor 237 is connected to the power supply voltage VDD, and the other end side thereof is connected to one end side of the pixel output switch 238. A signal subjected to the voltage conversion by the charge conversion unit 233 (imaging signal or signal at the resetting) is input to a gate thereof. The pixel output switch 238 outputs the signal subjected to the voltage conversion by the charge conversion unit 233 to the vertical transfer line 239. The other end side of the pixel output switch 238 is connected to the vertical transfer line 239 and a signal line, to which the pulsed drive signal φX is supplied, is connected to a gate thereof. When the pulsed drive signal φX is supplied from the vertical scanning unit 241 via the pixel drive line to the gate of the pixel output switch 238, the pixel output switch 238 is turned into an ON state, and the imaging signal or the signal at the resetting is transferred to the vertical transfer line 239.

One end side of the constant current source 242 is connected to the vertical transfer line 239, the other end side thereof is connected to the ground VSS, and a bias voltage Vbias1 is applied to a gate thereof. The unit pixel 230 is driven by the constant current source 242 and output of the unit pixel 230 is read out to the vertical transfer line 239. The signal read out to the vertical transfer line 239 is input to the noise elimination unit 243.

The noise elimination unit 243 includes a transfer capacitor (AC coupling condenser) 252 and a clamp switch (transistor) 253. One end side of the transfer capacitor 252 is connected to the vertical transfer line 239, and the other end side thereof is connected to the column source follower transistor 244. One end side of the clamp switch 253 is connected to a signal line, to which a clamp voltage Vclp is supplied from the reference voltage generating unit 246. The other end side of the clamp switch 253 is connected between the transfer capacitor 252 and the column source follower transistor 244, and the drive signal φVCL is input from the timing generating unit 25 to a gate thereof. The imaging signal input to the noise elimination unit 243 is a light-noise sum signal including a noise component.

When the drive signal φVCL is input from the timing generating unit 25 to the gate of the clamp switch 253, the clamp switch 253 is turned into an ON state, and the transfer capacitor 252 is reset by the clamp voltage Vclp supplied from the reference voltage generating unit 246. An imaging signal subjected to noise elimination by the noise elimination unit 243 is input to a gate of the column source follower transistor 244.

The noise elimination unit 243 does not require the condenser for sampling (sampling capacitor), and thus, a capacity of the transfer capacitor (AC coupling condenser) 252 may be a capacity sufficient with respect to an input capacity of the column source follower transistor 244. In addition, it is possible to decrease the area occupied by the noise elimination unit 243 in the first chip 21 since there is no sampling capacitor.

One end (drain) side of the column source follower transistor 244 is connected to the power supply voltage VDD, the other end (source) side thereof is connected to one end side of a column selection switch (second transfer unit) 254, and the imaging signal subjected to the noise elimination in the noise elimination unit 243 is input to the gate thereof. The voltage setting unit 247 is connected to the other end (source) side of the column source follower transistor 244.

The voltage setting unit 247 sets a potential (voltage) at the other end (source) side of the column source follower transistor 244 to a predetermined potential. The voltage setting unit 247 is provided with respect to the column source follower transistor 244 of each pixel column, and thus, it is possible to align the voltage (source voltage) of the other end (source) side of the column source follower transistor 244 of each column to a predetermined voltage.

In the example illustrated in FIG. 4, a current generating unit (current source) 470 configured by using a MOS transistor as the voltage setting unit 247 is connected to the other end (source) side of the column source follower transistor 244. The voltage setting unit 247 sets the voltage (source voltage) of the other end (source) side of the column source follower transistor 244 to a predetermined potential by causing a predetermined current to flow to the other end (source) side of the column source follower transistor 244. Incidentally, the current generating unit 470 may be configured by using a resistance or another constant current source, instead of the MOS transistor.

The current generating unit 470 causes a predetermined current to flow to the other end (source) side of the column source follower transistor 244 constantly at driving of the imaging unit 20, and accordingly, a voltage (source voltage) of the other end (source) side of the column source follower transistor 244 is constantly set to a predetermined potential. Incidentally, it is possible to set a period for which the voltage (source voltage) of the other end (source) side of the column source follower transistor 244 is set to the predetermined potential not to be constant, but to be only a period for which the charge photoelectrically converted by the photoelectric conversion element 231 is read out, or a period before or after, or only a period after the period for which the charge photoelectrically converted by the photoelectric conversion element 231 is read out. In this manner, it is possible to reduce power consumption by causing the current to flow only during a required period. Incidentally, in a case where the voltage setting unit 247 controls the period for which the voltage (source voltage) of the other end (source) side of the column source follower transistor 244 is set to the predetermined potential, for example, a switch or the like is provided such that the voltage setting unit 247 operates only when the drive signal φLSW illustrated in FIG. 7 to be described later is High.

Further, the leakage current assumed on the design is a Pico-ampere level, and in contrast, a predetermined current of a Nano-ampere level is caused to flow to the other end (source) side of the column source follower transistor 244 by the current generating unit 470. The voltage at the other end (source) side of the column source follower transistor 244 is not affected by variation caused by the leakage current by causing a high current, different from the leakage current, to flow, and thus, it is possible to prevent generation of shading or the like.

The one end side of the column selection switch 254 is connected to the other end side of the column source follower transistor 244, and the other end side thereof is connected to the horizontal transfer line (second transfer line) 258. A drive line for supplying the drive signal φHCLK<M> from the horizontal scanning unit 245 is connected to the gate of the column selection switch 254. When the drive signal φHCLK<M> is supplied from the horizontal scanning unit 245 to the gate of the column selection switch 254 of a column <M>, the column selection switch 254 is turned into an ON state, and a signal of the vertical transfer line 239 of the column <M> (imaging signal subjected to the noise elimination in the noise elimination unit 243) is transferred to the horizontal transfer line 258.

One end side of a constant current source 257 is connected to the horizontal transfer line 258, the other end side thereof is connected to the ground VSS, and a bias voltage Vbias2 is applied to a gate thereof. The constant current source 257 drives the column source follower transistor 244 and reads out the imaging signal from the vertical transfer line 239 to the horizontal transfer line 258. The signal read out to the horizontal transfer line 258 is input to a sampling and holding unit 255.

One end side of a horizontal reset transistor 256 is connected to a horizontal reset voltage Vclr, and the other end side thereof is connected to the horizontal transfer line 258. The drive signal φHCLR is input from the timing generating unit 25 to a gate of the horizontal reset transistor 256. When the drive signal φHCLR is input to the gate of the horizontal reset transistor 256 from the timing generating unit 25, the horizontal reset transistor 256 is turned into an ON state and the horizontal transfer line 258 is reset.

The sampling and holding unit 255 includes a buffer 261, a sampling and holding switch (transistor) 262, a sampling capacitor (condenser) 263, and an operational amplifier 264. The horizontal transfer line 258 is connected to an input side of the buffer 261, and the imaging signal and the noise signal at the horizontal resetting are input to the buffer 261 via the horizontal transfer line 258. An output of the buffer 261 is connected to one end side of the sampling and holding switch 262. The other end side of the sampling and holding switch 262 is connected to an input side of the operational amplifier 264. One end side of the sampling capacitor 263 is connected to the other end side of the sampling and holding switch 262 and the input side of the operational amplifier 264, and the other end side of the sampling capacitor 263 is connected to the ground VSS. An output of the operational amplifier 264 is connected to an inverting input terminal of the operational amplifier 264 and connected to an input side of the multiplexer 26. The sampling and holding unit 255 holds a voltage, immediately before the sampling and holding switch 262 is turned into an OFF state, in the sampling capacitor 263, and outputs the voltage held in the sampling capacitor 263 while the sampling and holding switch 262 is in the OFF state.

In the first embodiment, it is possible to suppress crosstalk of the imaging signal in the column direction by alternately performing the reading of the imaging signal subjected to the noise elimination from the vertical transfer line 239 and the resetting of the horizontal transfer line 258 by the horizontal reset transistor 256. Further, it is possible to output only the imaging signal subjected to the noise elimination to the operational amplifier 264 by turning the sampling and holding switch 262 of the sampling and holding unit 255 into an ON state when the imaging signal subjected to the noise elimination is transferred, and into the OFF state when the noise signal at the resetting is transferred. It is possible to halve a band of an amplification circuit at a subsequent stage and to suppress a range thereof by allowing the first chip 21 to include the sampling and holding unit 255.

The multiplexer 26 alternately outputs, to the output unit 31, the noise-eliminated imaging signal output from the sampling and holding unit 255 and the reference voltage Vref generated by the reference voltage generating unit 246. The output unit 31 performs signal amplification, if necessary, on the noise-eliminated imaging signal and the reference voltage Vref to alternately output the imaging signal and the reference voltage Vref to the second chip 22.

In the second chip 22, only the alternating current components of the noise-eliminated imaging signal and the reference voltage Vref are transmitted to the connector unit 5 via the transmission cable 3.

Figure 5:
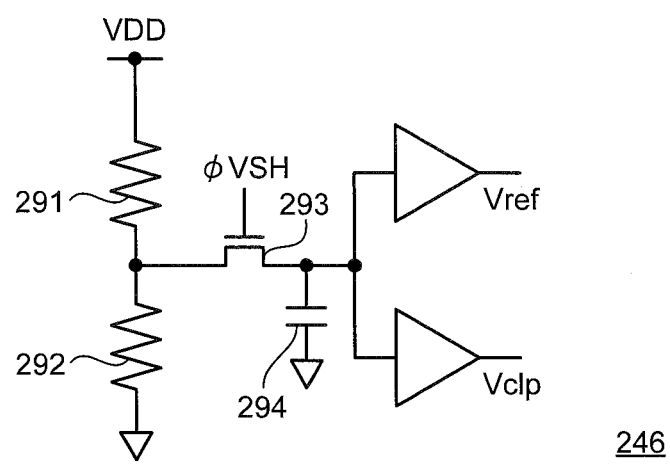
FIG. 5 is a circuit diagram illustrating a configuration of a reference voltage generating unit of the endoscope system according to the first embodiment.

FIG. 5 is a circuit diagram illustrating a configuration of the reference voltage generating unit of the light receiving unit of the endoscope system according to the first embodiment. The reference voltage generating unit (constant voltage signal generating unit) 246 includes a resistance voltage dividing circuit formed of two resistances 291 and 292, a switch (transistor) 293 driven by the drive signal ϕVSH, and a sampling capacitor (condenser) 294 for releasing from fluctuation independently of a power supply. The reference voltage generating unit 246 generates the reference voltage Vref (constant voltage signal) and the clamp voltage Vclp of the noise elimination unit 243 from the power supply voltage VDD at the timing in which the drive signal ϕVSH drives by driving of the switch 293.

Since the reference voltage Vref and the clamp voltage Vclp are generated at the same timing from the same power supply, the reference voltage Vref reflects the influence of power supply fluctuation with respect to the imaging signal output from the noise elimination unit 243. Further, the reference voltage Vref reflects transmission noise information in the transmission cable 3 during transmission. Accordingly, in the connector unit 5, it is possible to perform a noise eliminating process such as correlated double sampling to obtain an imaging signal, from which the noise during the transmission has been eliminated, by alternately transmitting the noise-eliminated imaging signal and the reference voltage Vref to the connector unit 5.

Figure 6A:
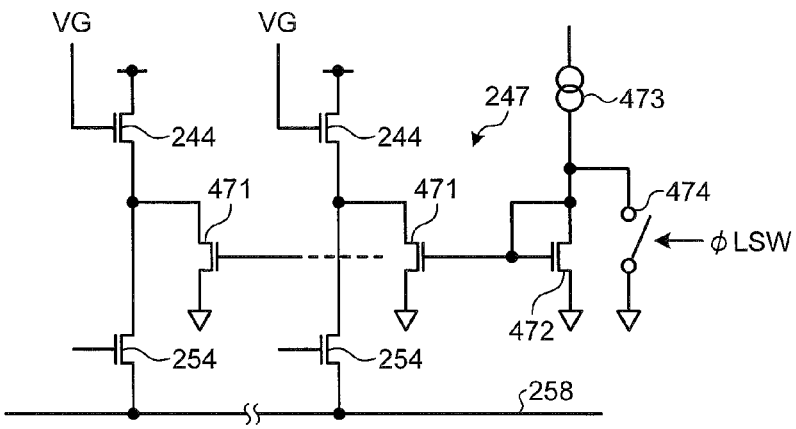
FIG. 6A is a circuit diagram illustrating a first another example of a voltage setting unit according to the first embodiment.

FIG. 6A is a circuit diagram illustrating a first another example of the voltage setting unit 247 according to the first embodiment. In the example illustrated in FIG. 6A, the voltage setting unit 247 is configured of a current mirror including an output-side transistor 471 and an input-side transistor 472, a current source 473 and a switch 474. One end (drain) of the output-side transistor 471 is connected to the other end (source) side of the column source follower transistor 244, and the other end (source) thereof is connected to the ground VSS. A gate of the output-side transistor 471 is connected with a gate of the input-side transistor 472. One end (drain) of the input-side transistor 472 is connected to the current source 473, and the other end (source) thereof is connected to the ground VSS. The switch 474 is connected between the one end (drain) of the input-side transistor 472 and the ground VSS. The switch 474 is controlled to be turned ON and OFF by the drive signal ϕLSW.

When the switch 474 is turned into an OFF state (the drive signal ϕLSW is High), a current supplied from the current source 473 flows, via the current mirror, to the other end (source) side of the column source follower transistor 244. In this manner, the voltage (source voltage) of the other end (source) side of the column source follower transistor 244 is set to the predetermined potential.

Figure 6B:
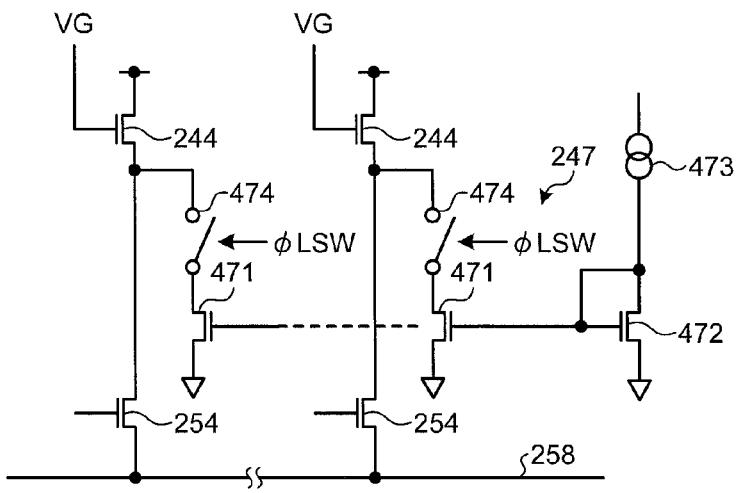
FIG. 6B is a circuit diagram illustrating a second another example of the voltage setting unit according to the first embodiment.

FIG. 6B is a circuit diagram illustrating a second another example of the voltage setting unit 247 according to the first embodiment. In the example illustrated in FIG. 6B, the switch 474 is provided between the other end (source) side of the column source follower transistor 244 and the output-side transistor 471. The other configurations and operations are the same as those in the example illustrated in FIG. 6A. When the switch 474 is turned into an ON state (the drive signal ϕLSW is High), the current supplied from the current source 473 flows, via the current mirror, to the other end (source) side of the column source follower transistor 244. In this manner, the voltage (source voltage) of the other end (source) side of the column source follower transistor 244 is set to the predetermined potential.

Figure 6C:
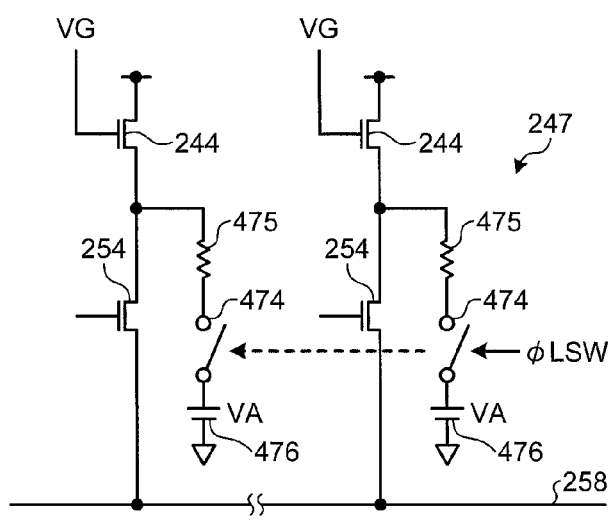
FIG. 6C is a circuit diagram illustrating a third another example of the voltage setting unit according to the first embodiment.

FIG. 6C is a circuit diagram illustrating a third another example of the voltage setting unit 247 according to the first embodiment. In the example illustrated in FIG. 6C, the voltage setting unit 247 is configured of a resistance 475, a DC voltage source 476 that supplies a predetermined voltage VA, and the switch 474. One end of the resistance 475 is connected to the other end (source) side of the column source follower transistor 244, and the other end thereof is connected to one end of the switch 474. The other end of the switch 474 is connected to one end of the DC voltage source 476, and the other end of the DC voltage source 476 is connected to the ground VSS.

When the switch 474 is turned into the ON state (the drive signal ϕLSW is High), the voltage VA supplied from the DC voltage source 476 is applied, via the resistance 475, to the other end (source) side of the column source follower transistor 244. In this manner, the voltage (source voltage) of the other end (source) side of the column source follower transistor 244 is set to the predetermined potential (the voltage VA).

The predetermined voltage (VA) is, for example, equal to or higher than the ground (VSS), and further is a voltage at which the column source follower transistor 244 operates in a linear region (a gate voltage (VG)–a threshold voltage (VTH) of the column source follower transistor 244), which is expressed by the following Formula (1).

$$VSS \leq VA \leq VG - VTH \tag{1}$$

Figure 7:
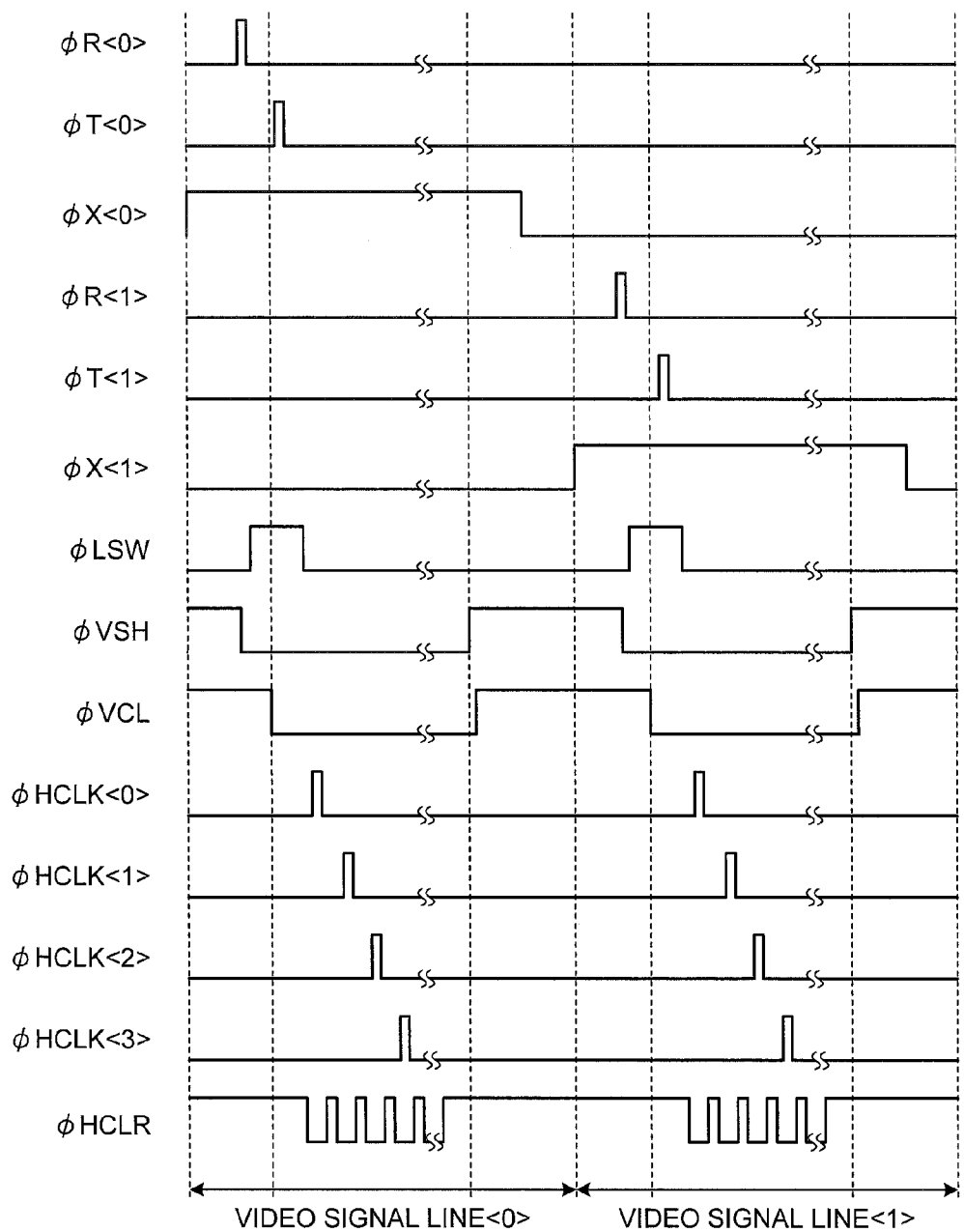
FIG. 7 is an example of a timing chart illustrating a drive signal of an imaging unit according to the first embodiment.

FIG. 7 is an example of a timing chart illustrating the drive signal of the imaging unit according to the first embodiment. In this example, a description will be made regarding a process from reading of a signal from the unit pixels 230 of a row <0> and a row <1> of the light receiving unit 23 until outputting the signal from the output unit 31. Further, the period for which the voltage setting unit 247 sets the voltage (source voltage) of the other end (source) side of the column source follower transistor 244 to the predetermined potential is not constant, but is only a period for which the charge photoelectrically converted by the photoelectric conversion element 231 is read out. Incidentally, even in the case where the voltage setting unit 247 is configured by the current source to cause the current to flow constantly, the timings of the drive signals other than the drive signal ϕLSW are the same, and the imaging unit 20 can be driven in the same manner.

Incidentally, in the timing chart illustrated in FIG. 7, the unit pixel 230 is configured to include only the photoelectric conversion element 231 for convenience of description. In a case where a plurality of the photoelectric conversion elements are included in the unit pixel 230, an operation for one video signal line illustrated in the timing chart is repeatedly performed as many as the number of the photoelectric conversion elements included in the unit pixel 230. That is, in a case where the photoelectric conversion elements 231 and 232 are included in the unit pixel 230 as in the first embodiment, the operation for one video signal line illustrated in this timing chart is repeated with respect to each of the transfer transistors 234 and 235, and accordingly, signals of the video signal lines <n> are read out.

First, the clamp switch 253 is turned ON (the drive signal ϕVCL is High), the pixel output switch 238 is turned ON (the drive signal ϕX<0> is High), the pixel reset unit 236 is turned ON in a pulsed form (the pulsed drive signal ϕR<0> is High), and the transfer transistor 234 is turned OFF (the pulsed drive signal φT<0> is Low) so that a noise signal including variation particular to the unit pixel 230 as an object of the reading, a noise at the pixel resetting and the like is output from the unit pixel 230 to the vertical transfer line 239. At this time, the gate of the column source follower transistor 244 is set to a voltage of the clamp voltage Vclp by keeping the clamp switch 253 in the ON state (the drive signal φVCL is High). The clamp voltage Vclp is determined at a falling timing of the drive signal φVSH and the reference voltage Vref is also determined at this timing.

Next, a signal, obtained by converting the charge photoelectrically converted in the photoelectric conversion element 231 by the charge conversion unit 233, is read out to the vertical transfer line 239 by turning the transfer transistor 234 ON in a pulsed form (the pulsed drive signal φT<0> is High) in a state in which the voltage setting unit 247 is activated (in the example illustrated in FIG. 6A, the switch 474 is turned into the OFF state by setting the drive signal φLSW to a Low level, and in the examples illustrated in FIGS. 6B and 6C, the switch 474 is turned into the ON state by setting the drive signal φLSW to a High level), and further the clamp switch 253 is turned into an OFF state (the drive signal φVCL is Low). In this state, since the pixel output switch 238 is still ON (the drive signal φX<0> is High), an imaging signal subjected to the voltage conversion by the charge conversion unit 233 (light-noise sum signal) is transferred to the vertical transfer line 239. According to this operation, an imaging signal (optical signal) from which a noise signal has been subtracted, is output to the gate of the column source follower transistor 244 via the transfer capacitor 252. Here, the signal output to the gate of the column source follower transistor 244 is a signal subjected to sampling using the clamp voltage Vclp as a reference.

After sampling the imaging signal using the clamp voltage Vclp as the reference, the horizontal reset transistor 256 is turned OFF (the drive signal φHCLR is Low), the resetting of the horizontal transfer line 258 is released, and the voltage setting unit 247 is deactivated (in the example illustrated in FIG. 6A, the switch 474 is turned into the ON state by setting the drive signal φLSW to the High level, and in the examples illustrated in FIGS. 6B and 6C, the switch 474 is turned into the OFF state by setting the drive signal φLSW to the Low level). In this manner, the voltage setting unit 247 sets the voltage (source voltage) at the other end (source) side of the column source follower transistor 244 to the predetermined potential.

Thereafter, the column selection switch 254 of a column <0> is turned ON (the pulsed drive signal φHCLK<0> is High) so as to transfer the imaging signal to the horizontal transfer line 258. At this time, the imaging signal is sampled by the sampling capacitor 263 by turning the sampling and holding switch 262 ON in a pulsed form (the pulsed drive signal φHSH is High). Thereafter, the imaging signal sampled by the sampling capacitor 263 is output to the output unit 31 by applying the pulsed drive signal φMUXSEL (FIG. 4) of a Low level to the multiplexer 26. At this time, in synchronization with the pulsed drive signal of the multiplexer 26, the horizontal reset transistor 256 is turned ON (the pulsed drive signal φHCLR is High), and the horizontal transfer line 258 is reset again.

In addition, thereafter, the pulsed drive signal φMUXSEL (FIG. 4) of a High level is applied to the multiplexer 26, the reference voltage Vref (constant voltage signal) generated by the reference voltage generating unit 246 is output to the output unit 31, the horizontal reset transistor 256 is turned OFF (the drive signal φHCLR is Low), the resetting of the horizontal transfer line 258 that has been reset is released, and the column selection switch 254 of the next column is turned ON (the drive signal φHCLK<1> is High), thereby transferring the imaging signal to the horizontal transfer line 258. At this time, the imaging signal is sampled by the sampling capacitor 263 by turning the sampling and holding switch 262 ON in a pulsed form (the pulsed drive signal φHSH (FIG. 4) is High). Then, the horizontal reset transistor 256 is turned ON (the drive signal φHCLR is High), the horizontal transfer line 258 is reset again, the pulsed drive signal φMUXSEL (FIG. 4) of a Low level is applied to the multiplexer 26 in synchronization with the pulse of the horizontal reset transistor 256, and the sampled imaging signal is output to the output unit 31.

When every image signal of the row <0> is transferred to the horizontal transfer line 258, the drive signal φVSH and the drive signal φVCL are set to the High level, and thereafter, the pixel output switch 238 is turned OFF (the drive signal φX<0> is Low). Accordingly, the transfer of the imaging signals of the row <0> is ended, and transfer of image signals of the next row <1> is initiated.

Such an operation is repeated as many times as the number of columns of the light receiving unit 23 (or the number of columns required to be read out), and accordingly, the imaging signal and the reference voltage Vref are alternately output from the output unit 31. Further, image signals for one frame are output by repeating the reading operations for one line as many times as the number of unit pixel rows (or the number of rows required to be read out).

As described above, according to the first embodiment of the present invention, the noise elimination unit 243 does not require a condenser for sampling (a sampling capacitor), and thus, it is possible to suppress a capacity of the transfer capacitor (AC coupling condenser) 252 to be low. Further, since there is no sampling capacitor, it is possible to decrease the area occupied by the noise elimination unit 243.

Further, according to the first embodiment of the present invention, the voltage setting unit 247 sets the voltage (source voltage) of the other end (source) side of the column source follower transistor 244 to the predetermined potential at least while the charge is read out from the respective photoelectric conversion elements 231 and 232, and thus the voltage of the other end (source) side of the column source follower transistor 244 is not affected by the variation caused by the leakage current. Accordingly, it is possible to prevent the generation of the shading or the like.

In addition, according to the first embodiment of the present invention, it is possible to alternately output the imaging signal and the reference voltage Vref for each pixel. In this manner, for example, it is possible to effectively eliminate an in-phase noise superimposed during transmission of a signal in a correlated double sampling circuit provided in the connector unit 5.

Incidentally, although the unit cell is configured of the pair of two photoelectric conversion elements 231 and 232 adjacent to each other in the column direction in the above-described first embodiment, a unit cell may be configured of a pair of two photoelectric conversion elements adjacent to each other in the row direction, or a unit cell may be configured of a set of four photoelectric conversion elements adjacent to one another in the row direction and column direction. Further, a unit cell may be configured of a single photoelectric conversion element without sharing pixels.

Incidentally, the sampling and holding unit 255 may be omitted. Even in a case in which the sampling and holding unit 255 is omitted, only the imaging signal is selected by the multiplexer 26 at the subsequent stage, and the imaging signal and the reference voltage Vref are alternately output to the output unit 31.

Figure 8:
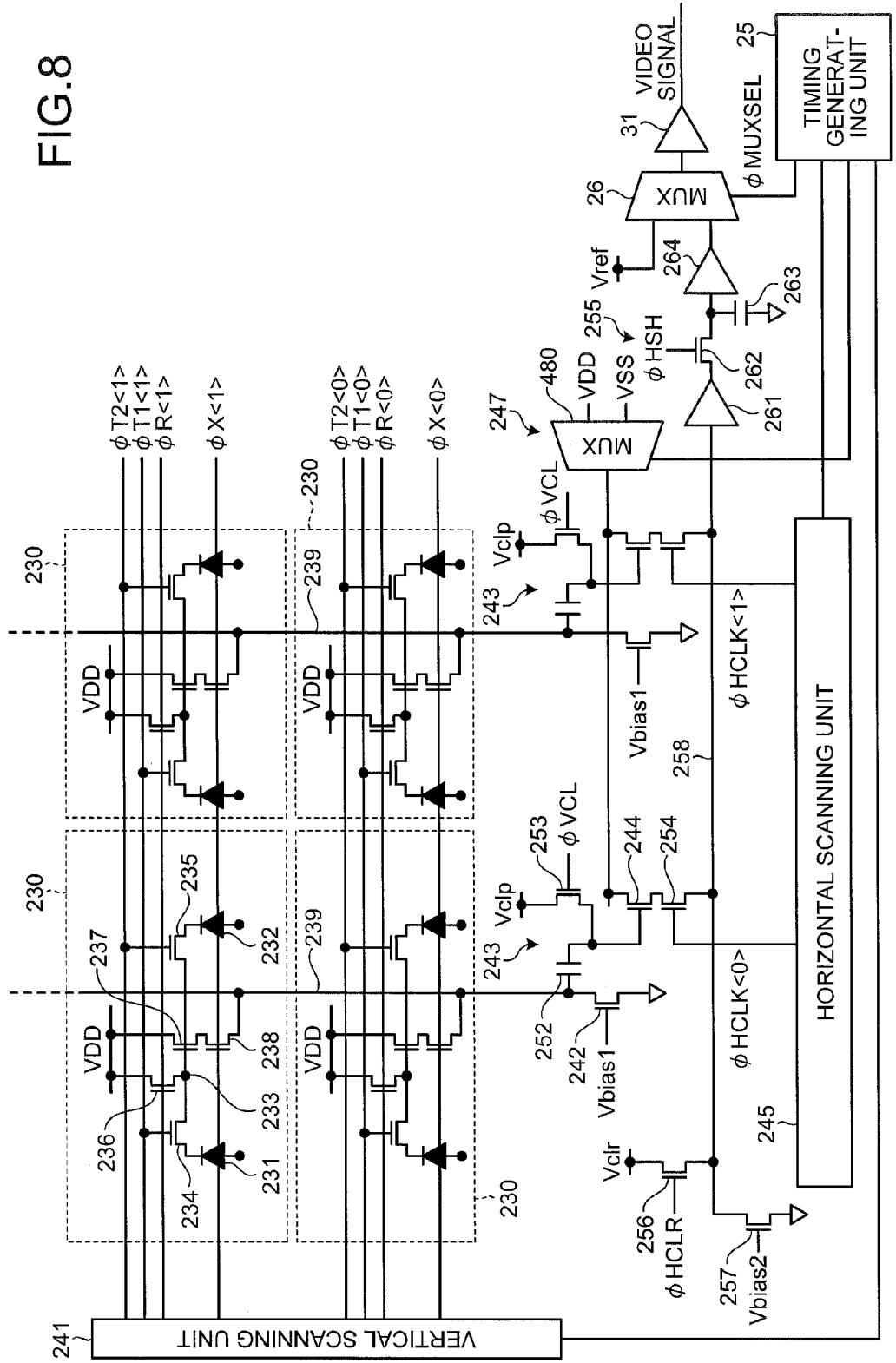
FIG. 8 is a circuit diagram illustrating a configuration of a first chip of an endoscope system according to a second embodiment.

FIG. 8 is a circuit diagram illustrating a configuration of a first chip of an endoscope system according to a second embodiment. In a description of the endoscope system 1 according to the second embodiment, the same reference numerals will be attached to the same constituent elements as those of the endoscope system 1 according to the first embodiment, and detailed descriptions thereof will be omitted.

In the second embodiment, the voltage setting unit 247 is replaced by a voltage switching unit 480 that switches the power supply voltage of the column source follower transistor 244. The other circuit configurations are the same as in first embodiment.

The voltage switching unit 480 is configured by, for example, using a multiplexer or a switch, and selectively supplies, as the power supply voltage of the column source follower transistor 244, any one between the power supply voltage VDD or the ground VSS according to the drive signal φLSW supplied from the timing generating unit 25. The voltage switching unit 480 supplies the power supply voltage VDD when the drive signal φLSW is the Low level, and supplies the ground VSS when the drive signal φLSW is the High level.

When the ground VSS is supplied as the power supply voltage of the column source follower transistor 244, the column source follower transistor 244 is turned into an ON state, and the voltage (source voltage) of the other end (source) side of the column source follower transistor 244 is set to the predetermined voltage at return from the ground VSS to the power supply voltage VDD. Incidentally, the ground VSS supplied as a driving voltage of the column source follower transistor 244 may be a voltage sufficiently low for turning the column source follower transistor 244 into the ON state, and for example, may be the predetermined voltage VA expressed by the above-described Formula (1).

In the second embodiment, similarly to the first embodiment, the voltage (source voltage) of the other end (source) side is set to the predetermined voltage by turning the column source follower transistor 244 into the ON state to cause the current to flow to the other end (source) side of the column source follower transistor 244. Accordingly, similarly to the first embodiment, the voltage of the other end (source) side of the column source follower transistor 244 is not affected by the variation caused by the leakage current also in the second embodiment. Accordingly, it is possible to prevent the generation of the shading or the like. It is possible to obtain the same effect as in the first embodiment, also in the second embodiment.

Further, in the second embodiment, the voltage switching unit 480 supplies the power supply voltage VDD as the power supply voltage of the column source follower transistor 244 while the charge is read out from each of the photoelectric conversion elements 231 and 232, and supplies the ground VSS for a period other than the period of reading out the charge. Detailed timing thereof will be described later with reference to FIGS. 10 and 11.

Figure 9:
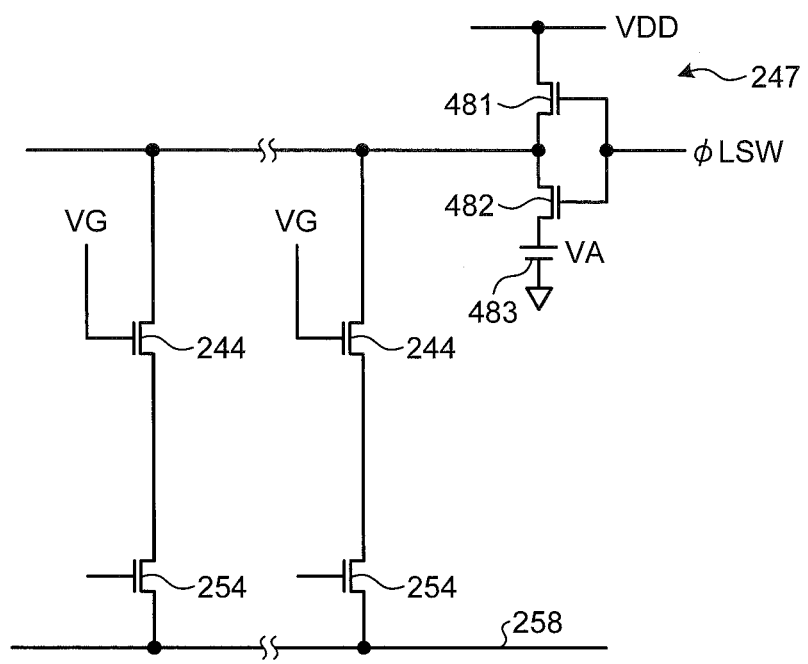
FIG. 9 is a circuit diagram illustrating another example of a voltage setting unit according to the second embodiment.

FIG. 9 is a circuit diagram illustrating another example of the voltage setting unit according to the second embodiment. In the example illustrated in FIG. 9, a voltage switching circuit configured of a PMOS transistor 481, an NMOS transistor 482, and a DC voltage source 483 is provided as the voltage setting unit 247. The DC voltage source 483 is a voltage source that supplies the predetermined voltage VA expressed by the above-described Formula (1), and supplies the predetermined voltage VA to the one end (drain) side of the column source follower transistor 244 when the drive signal φLSW is the High level. When the drive signal φLSW is the Low level, the power supply voltage VDD is supplied to the one end (drain) side of the column source follower transistor 244.

Figure 10:
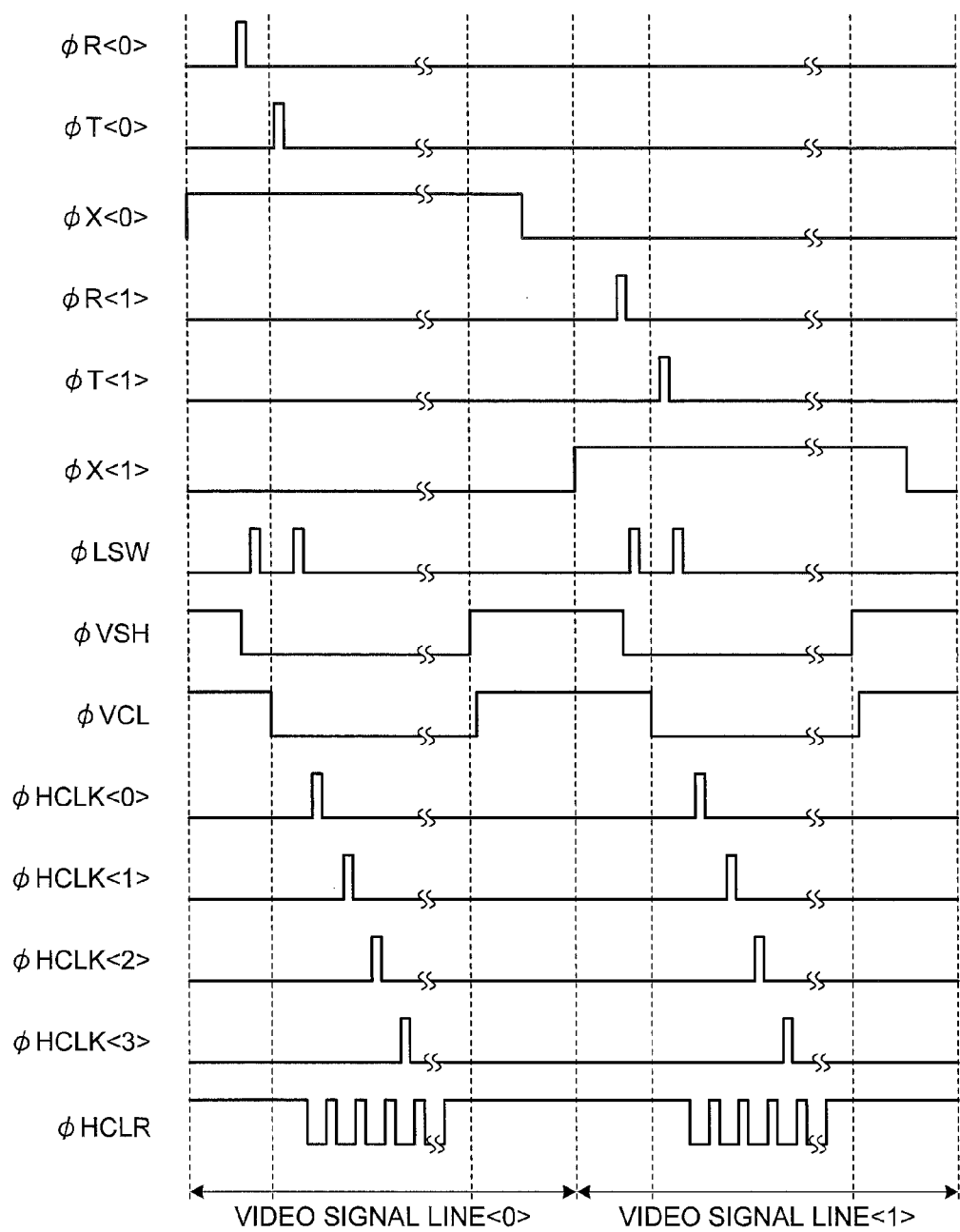
FIG. 10 is an example of a timing chart illustrating a drive signal of an imaging device according to the second embodiment.

FIG. 10 is an example of a timing chart illustrating the drive signal of the imaging unit according to the second embodiment. In this example, the period for which the voltage setting unit 247 sets the voltage (source voltage) of the other end (source) side of the column source follower transistor 244 to the predetermined potential is before or after the period for which the charge photoelectrically converted by the photoelectric conversion element 231 is read out. The other timings of the drive signals are the same as in the example illustrated in FIG. 7.

In the timing chart illustrated in FIG. 10, the voltage switching unit 480 supplies the ground VSS (or the predetermined voltage VA) to the one end (drain) side of the column source follower transistor 244 according to the pulsed drive signal φLSW after the pixel reset unit 236 is turned ON in a pulsed form (the pulsed drive signal φR<0> is High). In this manner, the voltage (source voltage) of the other end (source) side of the column source follower transistor 244 is aligned to be the predetermined potential, and the transfer transistor 234 is turned ON in a pulsed form (the pulsed drive signal φT<0> is High), and thus, a signal obtained by converting the charge, electrically converted in the photoelectric conversion element 231, by the charge conversion unit 233 is read out to the vertical transfer line 239. Thereafter, the voltage switching unit 480 supplies the ground VSS (or the predetermined voltage VA) to the one end (drain) side of the column source follower transistor 244 again, according to the pulsed drive signal φLSW so as to align the voltage (source voltage) of the other end (source) side of the column source follower transistor 244 to the predetermined potential, and the column selection switches 254 of each column are turned ON in order, thereby reading out the imaging signal to the horizontal transfer line 258.

Figure 11:
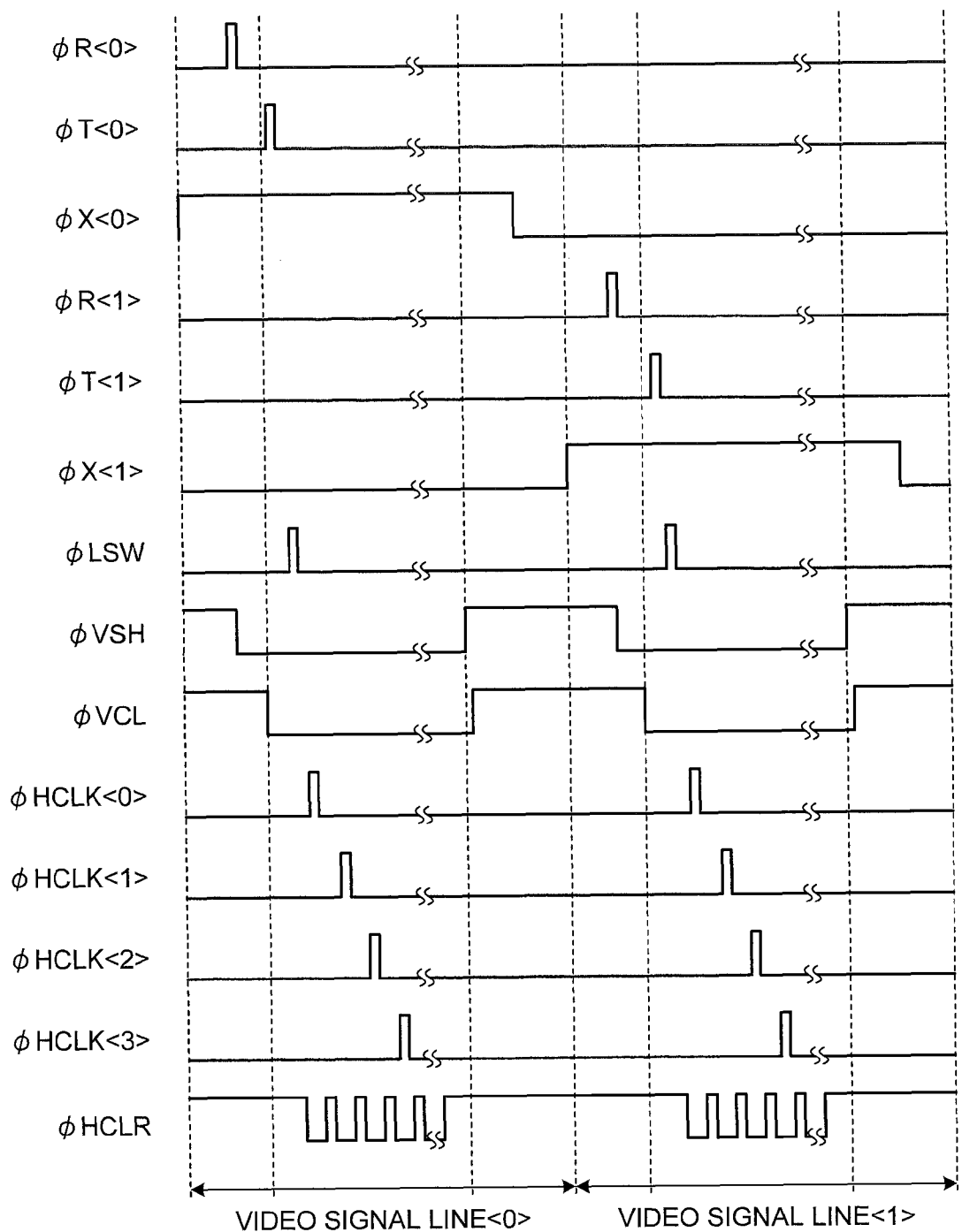
FIG. 11 is another example of the timing chart illustrating the drive signal of the imaging device according to the second embodiment.
Figure 12:
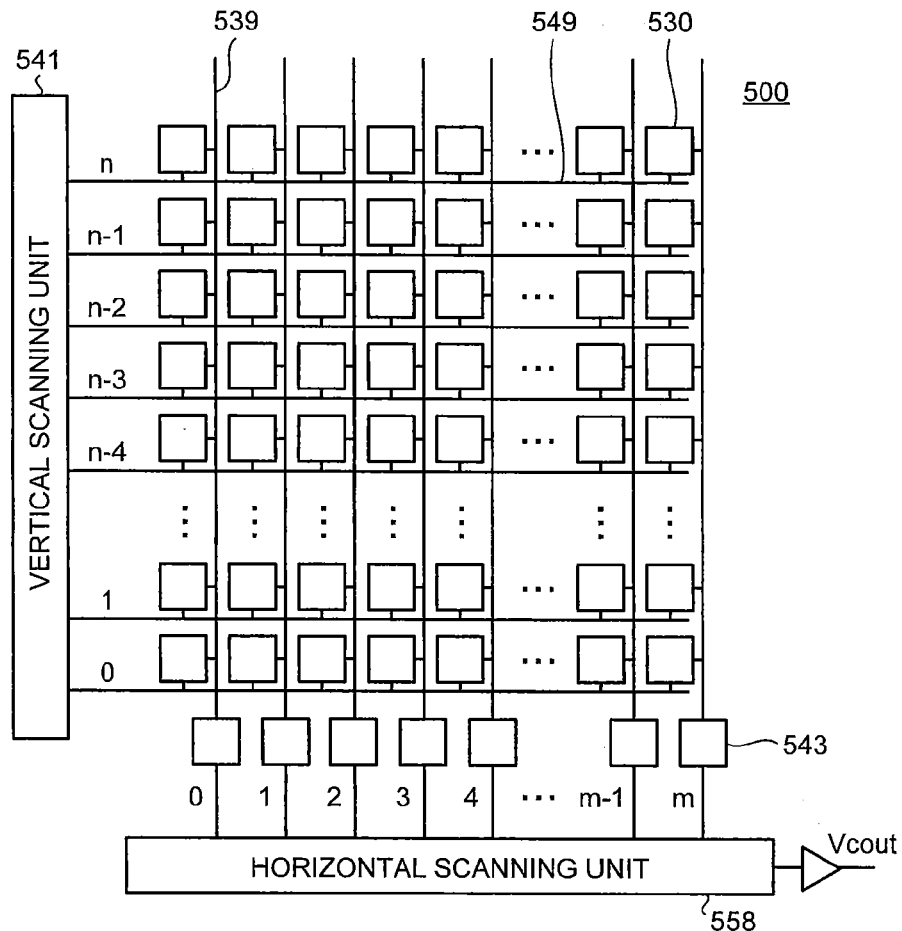
FIG. 12 is a circuit diagram illustrating a configuration of a conventional imaging device.
Figure 13:
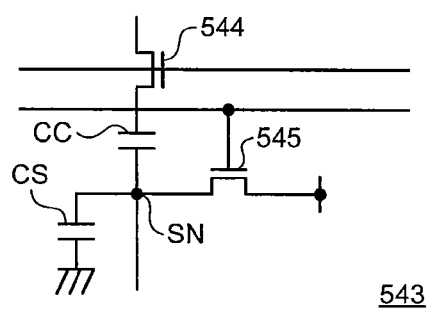
FIG. 13 is a circuit diagram representing a configuration of a noise elimination unit of the imaging device illustrated in FIG. 12.

FIG. 11 is another example of the timing chart illustrating the drive signal of the imaging unit according to the second embodiment. In this example, the period for which the voltage setting unit 247 sets the voltage (source voltage) of the other end (source) side of the column source follower transistor 244 to the predetermined potential is after the period for which the charge photoelectrically converted by the photoelectric conversion element 231 is read out. The other timings of the drive signals are the same as in the example illustrated in FIG. 10.

In the timing chart illustrated in FIG. 11, the pixel reset unit 236 is turned ON in a pulsed form (the pulsed drive signal φR<0> is High), and then the transfer transistor 234 is turned ON in a pulsed form (the pulsed drive signal φT<0> is High), and thus, the signal obtained by converting the charge, electrically converted in the photoelectric conversion element 231, by the charge conversion unit 233 is read out to the vertical transfer line 239. Thereafter, the voltage switching unit 480 supplies the ground VSS (or the predetermined voltage VA) to the column source follower transistor 244 again, according to the pulsed drive signal φLSW so as to align the voltage (source voltage) of the other end (source) side of the column source follower transistor 244 to the predetermined potential, and the column selection switches 254 of each column are turned ON in order, thereby reading out the imaging signal to the horizontal transfer line 258.

Incidentally, in the timing charts illustrated in FIGS. 7, 10 and 11, the voltage (source voltage) of the other end (source) side of the column source follower transistor 244 is set to the predetermined potential only one time before the imaging signal of the first column <0> of each video signal line is transferred to the horizontal transfer line 258, but the voltage (source voltage) of the other end (source) side of the column source follower transistor 244 may be set to the predetermined potential before the image signal of each column is transferred to the horizontal transfer line 258. Further, the voltage (source voltage) of the other end (source) side of the column source follower transistor 244 may be set to the predetermined potential in an arbitrary period, for example, for every other row, every other two rows, or the like.

It is possible to provide an imaging element, an imaging device and an endoscope system capable of achieving miniaturization without deterioration in image quality.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging element comprising:
   a plurality of pixels arranged in a two-dimensional matrix form, configured to receive light from outside, and configured to generate and output an imaging signal depending on an amount of the light received;
   a first transfer line connected to the pixels and configured to transfer the imaging signal;
   a second transfer line to which the imaging signal transferred by the first transfer line is output;
   a column selection switch configured to select one pixel column among the two-dimensional matrix, and output the imaging signal transferred by the first transfer line to the second transfer line;
   a column source follower including a gate to which the imaging signal transferred by the first transfer line is input, a drain end being connected to a power supply voltage, and a source end being connected to the column selection switch;
   a constant current source configured to drive the column source follower and read out the imaging signal transferred by the first transfer line to the second transfer line; and
   a current generating unit configured to flow a predetermined current to the source end side of the column source follower to absorb, by the column selection switch, an influence of noise caused by a leakage current.

2. The imaging element according to claim 1, wherein the current generating unit is configured to flow the predetermined current during: only a period the imaging signal is transferred to the first transfer line; or a predetermined period when the imaging signal is not transferred from the first transfer line to the second transfer line.

3. The imaging element according to claim 1, wherein the pixel includes:
   a photoelectric conversion element configured to perform photoelectric conversion depending on the amount of the light received and accumulate a charge;
   a first transfer unit configured to transfer the accumulated charge;
   a charge conversion unit configured to convert the transferred charge to a voltage or a current signal;
   a pixel reset unit configured to reset the charge conversion unit to a first voltage; and
   a signal output unit configured to output the converted signal, and
   the imaging element further comprising:
   a transfer capacitor connected to the first transfer line;
   a transfer capacitor reset unit configured to reset the transfer capacitor to a second voltage; and
   a drive unit configured to output a signal from the first transfer line by a noise signal reading operation in which the transfer capacitor is reset by the transfer capacitor reset unit at a time the signal of the charge conversion unit is output to the first transfer line via the signal output unit after the first transfer unit is turned into an OFF state and the charge conversion unit is reset by the pixel reset unit, and by a light-noise sum signal reading operation in which the signal of the charge conversion unit is output to the first transfer line via the signal output unit after the transfer capacitor reset unit is turned into an OFF state, the first transfer unit is turned into an ON state, and the charge accumulated by the photoelectric conversion element is transferred.

4. The imaging element according to claim 1, wherein the current generating unit is configured to set a potential of the source end side of the column source follower to a predetermined potential before the column selection switch is turned ON.

5. The imaging element according to claim 1, wherein the current generating unit is configured to set a potential of the source end side of the column source follower to a predetermined potential by a current flowing in the current generating unit.

6. The imaging element according to claim 5, wherein the current generating unit includes a MOS transistor.

7. The imaging element according to claim 5, wherein the current generating unit includes a resistance.

8. An imaging device comprising an imaging element including:
   a plurality of pixels arranged in a two-dimensional matrix form, configured to receive light from outside, and configured to generate and output an imaging signal depending on an amount of the light received;
   a first transfer line connected to the pixels and configured to transfer the imaging signal;
   a second transfer line to which the imaging signal transferred by the first transfer line is output;
   a column selection switch configured to select one pixel column among the two-dimensional matrix, and output the imaging signal transferred by the first transfer line to the second transfer line;
   a column source follower including a gate to which the imaging signal transferred by the first transfer line is input, a drain end being connected to a power supply voltage, and a source end being connected to the column selection switch;
   a constant current source configured to drive the column source follower and read out the imaging signal transferred by the first transfer line to the second transfer line; and
   a current generating unit configured to flow a predetermined current to the source end side of the column source follower to absorb, by the column selection switch, an influence of noise caused by a leakage current.

9. An endoscope system comprising an imaging element including:
- a plurality of pixels arranged in a two-dimensional matrix form, configured to receive light from outside, and configured to generate and output an imaging signal depending on an amount of the light received;
- a first transfer line connected to the pixels and configured to transfer the imaging signal;
- a second transfer line to which the imaging signal transferred by the first transfer line is output;
- a column selection switch configured to select one pixel column among the two-dimensional matrix, and output the imaging signal transferred by the first transfer line to the second transfer line;
- a column source follower including a gate to which the imaging signal transferred by the first transfer line is input, a drain end being connected to a power supply voltage, and a source end being connected to the column selection switch; a constant current source configured to drive the column source follower and read out the imaging signal transferred by the first transfer line to the second transfer line; and
- a current generating unit configured to flow a predetermined current to the source end side of the column source follower to absorb, by the column selection switch, an influence of noise caused by a leakage current.

* * * * *